(12) United States Patent
Ruiz Ballesteros et al.

(10) Patent No.: US 11,371,493 B2
(45) Date of Patent: Jun. 28, 2022

(54) DEVICE FOR DISPENSING A SUBSTANCE COMPRISING A CHAMBER DEFINING A SUBSTANCE INLET, A SUBSTANCE OUTLET, AN AIR INLET, AND AN AIR OUTLET, A PISTON LOCATED INSIDE THE CHAMBER AND WHOSE MOVEMENT CAUSES THE EXIT OF BOTH THE SUBSTANCE AND AIR TO OUTSIDE OF THE DEVICE

(71) Applicant: ZOBELE HOLDING SPA, Trento (IT)

(72) Inventors: Julio Cesar Ruiz Ballesteros, Barcelona (ES); Edoardo Bertassi, Trento (IT); Stefano Baldessari, Trento (IT)

(73) Assignee: ZOBELE HOLDING S.p.A., Trento (IT)

( * ) Notice: Subject to any disclaimer, the term of this patent is extended or adjusted under 35 U.S.C. 154(b) by 0 days.

(21) Appl. No.: 15/026,940

(22) PCT Filed: Oct. 3, 2013

(86) PCT No.: PCT/EP2013/070630
§ 371 (c)(1),
(2) Date: Apr. 1, 2016

(87) PCT Pub. No.: WO2015/049004
PCT Pub. Date: Apr. 9, 2015

(65) Prior Publication Data
US 2016/0298613 A1    Oct. 13, 2016

(51) Int. Cl.
*F04B 9/04*    (2006.01)
*A47K 5/12*    (2006.01)
*F04B 17/03*    (2006.01)
*B05B 11/00*    (2006.01)
(Continued)

(52) U.S. Cl.
CPC ............ *F04B 9/047* (2013.01); *A47K 5/1204* (2013.01); *A47K 5/1217* (2013.01); *A61L 9/14* (2013.01);
(Continued)

(58) Field of Classification Search
CPC .. F04B 9/047; F04B 19/06; F04B 9/04; F04B 13/00; F04B 17/03; B05B 11/3001;
(Continued)

(56) References Cited

U.S. PATENT DOCUMENTS 2,416,361 A * 2/1947 Trexler .................... B67D 7/08
222/63
4,712,983 A * 12/1987 Moynihan ................. F04B 9/02
417/234
(Continued)

FOREIGN PATENT DOCUMENTS

DE    4105379 A1    8/1992
IT    1236619 B     3/1993

OTHER PUBLICATIONS

International Search Report and Written Opinion, from PCT/EP2013/070630 with an international filing date of Oct. 3, 2013, dated Jun. 30, 2014, 11 pgs., mailed from European Patent Office, Rijswijk, The Netherlands.

*Primary Examiner* — Devon C Kramer
*Assistant Examiner* — Benjamin Doyle
(74) *Attorney, Agent, or Firm* — BakerHostetler

(57) ABSTRACT

The device comprises a chamber (1) provided with an inlet (2) and an outlet (3); a piston (4) inside the chamber (1), the movement of which causes the exit of the substance; and a motor (5) with an output shaft (6) that drives the motion of said piston (4) when it receives a signal from a sensor; and transmission means that transmit the drive movement from the motor (5) to said piston (4); characterised in that said
(Continued)

transmission means comprise: a worm gear (7) rotationally attached to the output shaft (6) of the motor (5); a first transmission element (8) connected to said piston (4); and a second transmission element (9) connected to said worm gear (7) and to said first transmission element (8).

The device enables small dimensions compared to conventional devices.

3 Claims, 2 Drawing Sheets

(51) Int. Cl.
    *F04B 19/06*     (2006.01)
    *F04B 13/00*     (2006.01)
    *A61L 9/14*     (2006.01)

(52) U.S. Cl.
    CPC .......... *B05B 11/3001* (2013.01); *F04B 13/00* (2013.01); *F04B 17/03* (2013.01); *F04B 19/06* (2013.01); *A61L 2209/134* (2013.01)

(58) Field of Classification Search
    CPC ... A61L 9/14; A61L 2209/134; A47K 5/1217; A47K 5/1204
    USPC .......................................................... 417/415
    See application file for complete search history.

(56) References Cited

U.S. PATENT DOCUMENTS

| | | | |
|---|---|---|---|
| 5,092,749 A * | 3/1992 | Meijer | F04B 9/045 417/474 |
| 5,289,952 A * | 3/1994 | Gueret | B05B 7/0037 222/190 |
| 5,397,144 A | 3/1995 | Mirand et al. | |
| 5,445,288 A * | 8/1995 | Banks | B05B 7/0025 222/95 |
| 5,647,733 A * | 7/1997 | Augustyn | F04B 43/009 417/360 |
| 6,062,428 A * | 5/2000 | Callahan | B67D 7/0227 222/387 |
| 6,082,586 A * | 7/2000 | Banks | B05B 11/3087 222/95 |
| 6,209,752 B1 * | 4/2001 | Mitchell | A47K 5/1215 222/181.3 |
| 6,357,397 B1 * | 3/2002 | Kull | F01C 1/077 123/18 R |
| 6,439,104 B1 * | 8/2002 | Tonogai | F04B 35/01 74/29 |
| 6,793,105 B1 | 9/2004 | Ouyoung | |
| 7,325,704 B2 * | 2/2008 | Kasting | B05B 11/0032 222/321.4 |
| 7,611,030 B2 * | 11/2009 | Reynolds | A47K 5/1217 222/1 |
| 7,780,039 B2 * | 8/2010 | Criswell | B05B 11/3087 222/108 |
| 8,430,274 B2 * | 4/2013 | van der Heijden | B05B 11/3087 222/190 |
| 8,662,355 B2 * | 3/2014 | Spiegelberg | A47K 5/14 222/190 |
| 8,814,005 B2 * | 8/2014 | Banks | B05B 11/3015 222/190 |
| 9,101,952 B2 * | 8/2015 | McNulty | A47K 5/14 |
| 2015/0114992 A1 * | 4/2015 | dos Santos | F16N 13/02 222/63 |

* cited by examiner

DEVICE FOR DISPENSING A SUBSTANCE COMPRISING A CHAMBER DEFINING A SUBSTANCE INLET, A SUBSTANCE OUTLET, AN AIR INLET, AND AN AIR OUTLET, A PISTON LOCATED INSIDE THE CHAMBER AND WHOSE MOVEMENT CAUSES THE EXIT OF BOTH THE SUBSTANCE AND AIR TO OUTSIDE OF THE DEVICE

CROSS-REFERENCE TO RELATED APPLICATIONS

This application is a national stage of international application no. PCT/EP2013/070630, filed Oct. 3, 2013, the disclosure of which is incorporated herein by reference in its entirety.

The present invention relates to a device for dispensing substances, such as soap or air freshener, that dispenses a specific amount of said substance when a detector is activated, such as when a hand is placed near said dispensing device or when the presence of a person is detected.

BACKGROUND OF THE INVENTION

Devices are currently commonly used for dispensing substances, such as soap, that dispense a predetermined amount of substance using presence detectors, such as when a hand is detected near the device.

These dispensing devices comprise a motor actuated by a sensor that detects said presence, releasing the substance from the device by means of a transmission mechanism.

The dispensing devices of this type currently known are bulky, as said transmission means generally comprise a plurality of gears that occupy a great volume.

The volume occupied by these devices is a drawback when installing the devices, for example, in a bathroom, as the available space is limited.

In addition, the market requires said devices to have a competitive price that allows them to be accepted by consumers, so that the designers of these devices must provide the lowest possible price.

In practice, it is common to use a brush motor to achieve said competitive price. This type of motor has the advantage of a low price, but it has a high rotation speed that requires considerable mechanical gear reduction in order to obtain the appropriate speed and force for pumping the substance. This speed must not be so fast to make soap splash on the user's hands, for example, nor so slow to make the user impatient.

Consequently, there is a need for a device for dispensing substances, such as soap or air freshener, with dimensions as small as possible for use in locations with limited space, and with an affordable price, in line with user needs.

DESCRIPTION OF THE INVENTION

The dispensing device of the invention manages to solve the aforementioned drawbacks, and provides additional advantages as described below.

The device for dispensing substances of the present invention comprises:
a chamber with a substance inlet and outlet;
a piston inside said chamber that when actuated pushes said substance out of said chamber;
a motor provided with an output shaft that drives the movement of said piston when it receives a signal from a sensor; and
transmission means that transmit the drive movement from the motor to said piston;
and it is characterised in that said transmission means comprise:
a worm gear that turns with the output shaft of the motor;
a first transmission element connected to said piston; and
a second transmission element that is connected to said worm gear and said first transmission element, transmitting the rotation movement from said worm gear to said first transmission element.

According to a preferred embodiment, said first transmission element is connected to said piston by a pin of the first transmission element which is housed inside a groove of said piston, the rotation of said first transmission element resulting in the displacement of said pin inside the groove and the alternating linear motion of said piston.

Preferably, said piston comprises a cylinder in which the substances to be dispensed from the chamber are placed.

Optionally, said chamber also comprises an outside air inlet and an air outlet.

According to a preferred embodiment, said first transmission element is a disc comprising a toothed wheel with its teeth located on the perimeter of one of the disc faces, and said second transmission element comprises a first toothed wheel that engages the aforementioned wormed gear and a second toothed wheel that engages the first transmission element.

Advantageously, the diameter of said first toothed wheel of the second transmission element is smaller than the diameter of said second toothed wheel of the second transmission element, and the toothed wheel of the first transmission element and the second toothed wheel of the second transmission element are perpendicular to each other.

The dispensing device of the present invention has the advantage of having small dimensions compared to conventional dispensing devices of this type, which makes it suitable for use in any location, such as above a sink. In addition, its cost is appropriate for the users' needs.

BRIEF DESCRIPTION OF THE DRAWINGS

To aid a better understanding of the matters described above, some drawings are accompanied where, for purposes of illustration only and as a non-limiting example, a schematic representation is given of an embodiment of the invention.

DESCRIPTION OF A PREFERRED EMBODIMENT

Figure 1:
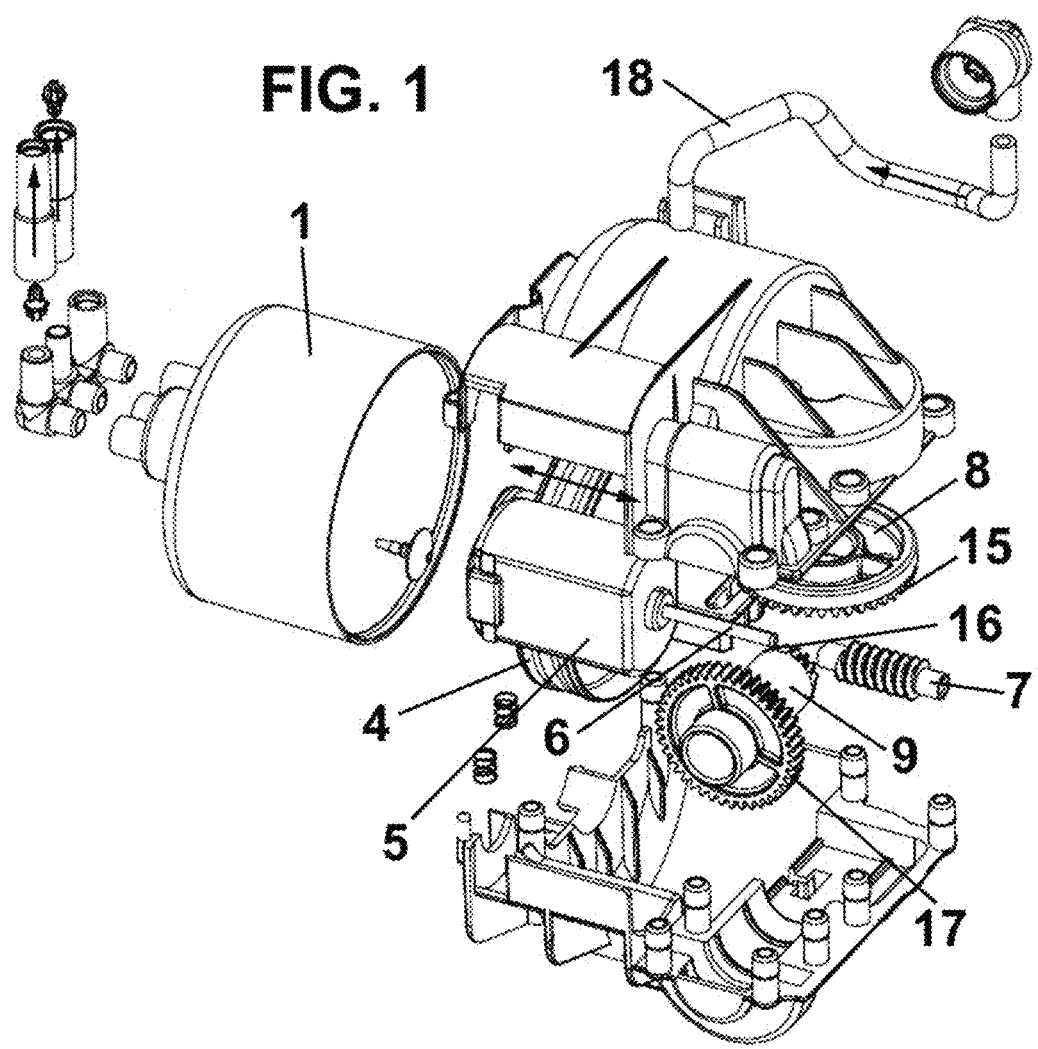
FIG. 1 is a perspective exploded view of the dispensing device of the present invention.

Firstly, it should be remarked that the dispensing device of the present invention is preferably used to dispense soap automatically when detecting the presence of a hand, although it is obvious that such a dispensing device could also be used to dispense other substances, such as air freshener when detecting the presence of a person.

The dispensing device of the present invention comprises a chamber 1 that contains the substance to dispense and air; inside this chamber 1, a piston 4 moves in an alternating motion to dispense said substance and/or air.

The movement of said piston 4 is driven by a motor 5 through motion transmission means.

Said transmission means comprise a worm gear 7 that turns together with the output shaft 6 of the motor 5, a first transmission element 8 formed by a disc comprising a toothed wheel 15, and a second transmission element 9 placed between said worm gear 7 and said first transmission element 8.

The second transmission element 9 comprises a first toothed wheel 16 that engages said worm gear 7 and a second toothed wheel 17 that engages the first transmission element 8, specifically its toothed wheel 15.

In addition, the first transmission element 8 comprises a pin 19 placed in said disc that is housed inside a groove 11 of the aforementioned piston 4. In this way, when the disc turns it will move the pin 10 inside the groove 11, displacing the piston 4 forward and backward inside the chamber 1.

Figure 2:
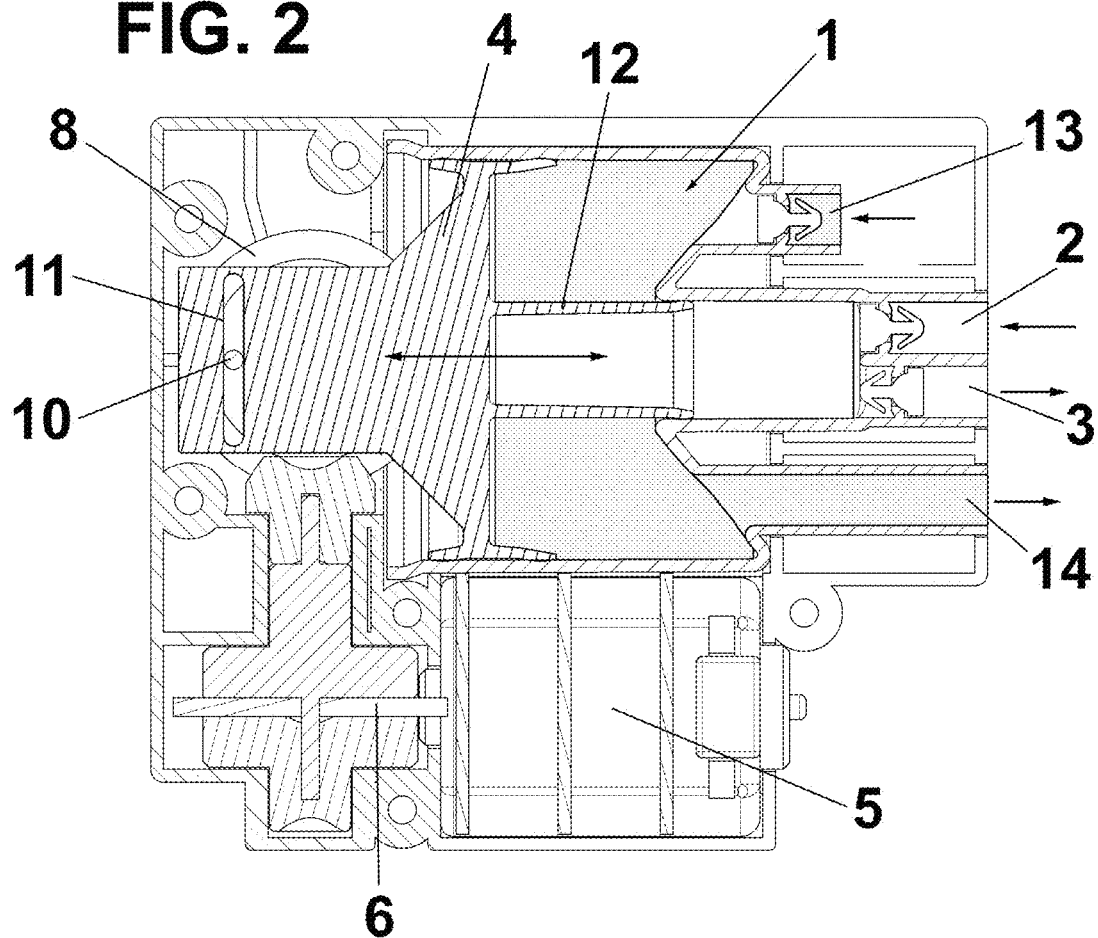
FIG. 2 is a cross-sectional view of the dispensing device of the present invention.

Said piston 4 comprises a cylinder 12 that defines a housing for the soap or substance inside the chamber 1, and also divides said chamber 1 into a compartment for air, around said cylinder 12, as shown in FIG. 2.

Said chamber 1 also comprises an substance inlet 2 and a substance outlet 3, as well as an air inlet 13 and an air outlet 14, all of them having the corresponding check valves.

Said substance, for example soap, is introduced in said chamber 1 though the inlet 2 from a refill (not shown in the figures) using a supply tube 18, as shown in FIG. 1. In addition, the substance outlet 3 and air outlet 14 can dispense the substance and/or air to the user directly, or preferably are supplied to a mixing chamber from where they are dispensed to the users.

The dispensing device of the present invention operates as follows:

When a sensor (not shown in the figures) detects the presence, for example, of a hand, it sends a signal to the motor 5, which will be actuated and turn its output shaft 6 for a specific number of turns, calculated according to the amount of soap or substance to be dispensed to the user This calculation will be performed using suitable conventional control means.

The rotation of the output shaft 6 of the motor 5 will cause the corresponding rotation of the worm gear 7, which in turn will cause the rotation of the second transmission element 9 and the first transmission element 8, through the corresponding toothed wheels 15, 16 and 17. This transmission of movement will, using the dimensions of the corresponding toothed wheels, result in the appropriate reduction in the speed of rotation in order to dispense the correct amount of substance.

When the first transmission element 8 turns, it causes the alternating displacement of said piston 4, as described above, so that the substance and/or air inside the chamber 1 is dispensed, and also causes the subsequent entry of substance and/or air into the chamber 1 during the alternating motion of the piston 4.

Although reference has been made to a specific embodiment of the invention, it will be obvious to a person skilled in the art that the dispensing device described can be susceptible to numerous variations and modifications, and that all the aforementioned details may be replaced by other technically equivalent ones, without extending beyond the scope of protection defined by the appending claims.

The invention claimed is:

1. A device for dispensing a substance, the device comprising:
   a chamber defining a substance inlet (2), a substance outlet (3), an air inlet (13) for the receipt of air from the outside, and an air outlet (14);
   a piston (4) located inside the chamber (1), the movement of which causes the exit of both (a) the substance to the outside of said device via said substance outlet (3) and (b) air to the outside of said device via said air outlet (14);
   a motor (5) provided with an output shaft (6) that drives the movement of said piston (4) when it receives a signal from a sensor; and
   transmission means that transmit the drive movement from the motor (5) to said piston (4);
   wherein said transmission means comprises:
   a worm gear (7) rotationally attached to the output shaft (6) of the motor (5);
   a first transmission element (8) connected to said piston by a pin (10) of said first transmission element (8) that is housed in a groove (11) of said piston (4), the rotation of said first transmission element (8) causing the displacement of said pin (10) longitudinally along and inside the groove (11), wherein the reciprocating movement of the pin (10) longitudinally along and inside the groove (11) causes the alternating linear movement of said piston (4), wherein said first transmission element (8) is a disc comprising a toothed wheel (15) with its teeth located at the perimeter of one of the faces of the disc;
   a second transmission element (9) that is connected to said worm gear (7) and to said first transmission element (8), transmitting the rotation from said worm gear (7) to said first transmission element (8), wherein said second transmission element (9) comprises a first toothed wheel (16) that engages said worm gear (7) and a second toothed wheel (17) that engages said first transmission element (8); and
   wherein said toothed wheel (15) of the first transmission element (8) comprises teeth spaced apart from one another along a first circumferential direction and said second toothed wheel (17) of the second transmission element (9) comprises teeth spaced apart from one another along a second circumferential direction different from the first circumferential direction, and
   wherein said toothed wheel (15) of the first transmission element (8) and said second toothed wheel (17) of the second transmission element (9) are perpendicular to each other with an axis of rotation of said toothed wheel (15) of the first transmission element (8) being perpendicular to an axis of rotation of said second toothed wheel (17) of the second transmission element (9) and said teeth of the toothed wheel (15) of the first transmission element (8) and said teeth of the second toothed wheel (17) of the second transmission element (9) directly engage each other, such that rotation of one of said toothed wheel (15) of the first transmission element (8) and said second toothed wheel (17) of the second transmission element (9) directly causes rotation of the other of said toothed wheel (15) of the first transmission element (8) and said second toothed wheel (17) of the second transmission element (9).

2. The device according to claim 1, wherein said piston (4) comprises a cylinder (12) in which are placed the substance for exit from said chamber (1).

3. The device according to claim 1, wherein the diameter of said first toothed wheel (16) of the second transmission element (9) is smaller than the diameter of said second toothed wheel (17) of the second transmission element (9).

\* \* \* \* \*